United States Patent [19]

Hunt et al.

[11] Patent Number: 4,478,729

[45] Date of Patent: Oct. 23, 1984

[54] MOLYBDENUM SULFONATES FOR FRICTION REDUCING ADDITIVES

[75] Inventors: Mack W. Hunt; Charles T. West, both of Naperville, Ill.

[73] Assignee: Standard Oil Company (Indiana), Chicago, Ill.

[21] Appl. No.: 388,047

[22] Filed: Jun. 14, 1982

[51] Int. Cl.$^3$ .......................... C10M 1/38; C10M 1/54
[52] U.S. Cl. .................................... 252/33.2; 252/46.4
[58] Field of Search .............................. 252/33.2, 46.4

[56] References Cited

U.S. PATENT DOCUMENTS 3,281,355 10/1966 Cyphers et al. .................... 252/46.4

*Primary Examiner*—Jacqueline V. Howard
*Attorney, Agent, or Firm*—James R. Wilson; William T. McClain; William H. Magidson

[57] ABSTRACT

Lubricating oil composition comprising the reaction product of (a) molybdenum sulfonate, which is the reaction product of a hydrocarbyl sulfonic acid compound and molybdenum halide, and (b) sulfur or a sulfur-yielding compound. Preferably, an alkyl sulfonic acid having from 8–200 carbon atoms in the alkyl group is reacted with molybdenum pentachloride, and the molybdenum sulfonate resulting therefrom is sulfurized to produce the reaction product of the invention.

11 Claims, No Drawings

MOLYBDENUM SULFONATES FOR FRICTION REDUCING ADDITIVES

BACKGROUND OF THE INVENTION

This invention relates to lubricating oil compositions comprising oil soluble sulfurized molybdenum sulfonate additives which are the sulfurized reaction product of a sulfonic acid compound and molybdenum halide. The reaction product is especially useful in lubricating oil compositions for reducing friction between moving parts.

Lubricating oil additives that improve operating properties of lubricating oil include dispersants, antioxidant additives, and friction modifiers that improve engine efficiency by reducing the friction between the moving parts in the engine. A large number of hydrocarbon-soluble molybdenum-containing compositions have been disclosed in recent years, including water-soluble molybdenum-amine complexes, W. F. Marzluff, *Inorg. Chem.* III, 345 (1964), molybdenum-oxazoline complexes, U.S. Pat. No. 4,176,074 Coupland, et al. and molybdenum lactone oxazoline complexes, U.S. Pat. No. 4,176,073 Ryer et al., molybdenum beta-keto esters, molybdenum-olefin-carbonyl complexes, molybdenum-amide complexes, molybdenum diorganophosphates, U.S. Pat. No. 4,178,258 Papay, et al., molybdenum organodithiophosphates, molybdenum carboxylates, molybdenum dithiocarbamates, etc.

A series of patents issued to King and De Vries and assigned to Chevron Research Company in 1981, disclose lubricating oil compositions incorporating antioxidant molybdenum compounds, these patents being U.S. Pat. Nos. 4,259,194, 4,259,195, 4,261,843, 4,263,152, 4,265,773, 4,272,387, 4,283,295, and 4,285,822. The inventors state that the precise molecular formula of these molecular compounds is not known, but they are believed to be compounds with molybdenum oxides or sulfides complexed by or the salt of one or more nitrogen atoms from a basic nitrogen-containing composition (such as, e.g., succinimide, carboxylic acid and Mannich bases) used to prepare the lubricant. A polar promotor to facilitate the interaction between the acidic molybdenum compound and basic nitrogen compound may be used, preferably ethylene glycol or water.

U.S. Pat. No. 3,047,500, Matson, discloses what the patentees believe to be a molybdenum disulfide formed in situ as a result of the interaction of a molybdenum phenolate and an oil-soluble organic sulfur compound. These two ingredients are added to a lubricant for extreme pressure protection, there being no chemical interaction between the molybdenum and sulfur until substantial heat has been generated on the work surface to produce the molybdenum sulfide. U.S. Pat. No. 4,266,945, Karn, discloses a friction modifying lubricant prepared by the reaction of an acid of molybdenum with a phenol or aldehyde condensation product and a primary or secondary amine. The compositions are stated to be especially useful when combined with active sulfur and an oil-soluble dispersant. U.S. Pat. No. 4,202,781, Sabol, et al., discloses a method of preparing a molybdenum phosphosulfurized hydrocarbon composition, the composition being useful as an oxidation inhibitor and friction modifier for lubricants of internal combustion engines. The reaction disclosed produces stable molybdenum-containing compositions without the use of high temperatures, ether-complexing solvents or hydrogen peroxide.

The molybdenum compounds produced by the methods of the above-noted patents, all of which are expressly incorporated by reference herein, potentially suffer from either economic inefficiencies or from changing product requirements. For instance, at least one major U.S. automobile manufacturer has specified a maximum level of 0.11 per cent phosphorus in motor oils used in internal combustion engines in 1983 and thereafter. Most commercially available oil-soluble molybdenum additives having antifriction properties in lubricating oil contain phosphorus in the form of phosphosulfurized hydrocarbons or thiophosphates. However, the most effective anti-wear additive commonly used in lubricating oils is a zinc-phosphorus composition, such as zinc dithiophosphate, which is useful in amounts to potentially account for the entire phosphorus "allotment" in lubricating oil. Therefore, a need exists for a molybdenum-containing additive which provides friction reduction properties at low cost without the use of phosphorus.

SUMMARY OF THE INVENTION

The improved lubricating oil composition of the present invention can be prepared by reacting a sulfonic acid compound with a molybdenum halide, the reaction product thereof being reacted with sulfur or a sulfur-yielding compound. The monovalent metal salts of the sulfonate also will react favorably under the reaction conditions described herein. Preferably, the molybdenum halide comprises molybdenum pentachloride, and the sulfonic acid compound comprises hydrocarbyl sulfonic acid, the hydrocarbyl group being an alkyl or alkaryl group containing from 8 to 200 carbon atoms. The additive prepared can be added to a lubricating oil to impart a molybdenum concentration of approximately 0.04 to 0.05 percent, by weight of the oil.

DETAILED DESCRIPTION OF THE INVENTION

A general object of this invention is to provide improved oil-soluble molybdenum-containing antifriction agents and lubricating oil compositions comprising these agents. Another object of the invention is to provide improved oil soluble molybdenum compositions that are relatively inexpensive to prepare and contain no phosphorus. Other objects appear hereinafter.

It has previously been proposed to make a molybdenum sulfonate for antifriction lubricating oil additives. However, molybdenum sulfonates contain sulfur in a highly oxidized state which effectively inactivates the sulfur in terms of producing a molybdenum sulfide in situ, generally considered a superior friction reduction agent when deposited on worked surfaces.

We have now found that the objects of this invention can be obtained with a molybdenum additive comprising the reaction product of a sulfonic acid compound and molybdenum halide which is thereafter sulfurized, and which, when added to a lubricating oil, provides excellent friction reducing properties. While we do not wish to be held to any theory as to the active molybdenum-containing reaction product, we believe that the increased friction reduction exhibited by lubricating oils containing the additive of the present invention is due to the formation of a thiomolybdenum sulfonate, from which a molybdenum sulfide film is deposited on the worked surfaces in an internal combustion engine.

In addition to its use as a lubricating oil additive, the molybdenum compounds of the present invention can find utility in certain self-lubricating or antiwear structures, in fuel additives, as mold release agents, and in iron and steel alloys.

Briefly, the molybdenum-containing compounds useful in preparing the novel lubricating oil additives of this invention are those molybdenum halides which react with the active hydrogen of sulfonic acids, including the molybdenum fluorides, chlorides, bromides, and iodides. In contrast to other molybdenum compounds, the molybdenum halides exhibit high reactivity with an easily broken molybdenum-halide bond.

The sulfonic acid compounds useful in preparing the novel lubricating oil additives of this invention are hydrocarbyl sulfonic acids, with representative hydrocarbyl groups such as benzene, naphthalene, alkyl or alkyl-aryl (alkaryl) groups, and the monovalent alkali metal salts thereof, such as $Li^+$, $Na^+$, $K^+$, and $NH_4^+$. Especially preferred are the alkyl and alkaryl sulfonic acids, with the alkyl group having from 8 to 200 carbon atoms. At this molecular weight the sulfonic acid compound remains relatively oil soluble and is easily combined with a lubricating oil. Below this molecular weight, oil solubility is substantially decreased, and above this molecular weight the dilution of the active molybdenum-containing additive renders the additive cost-ineffective. Preferably, the lowest practical molecular weight alkyl group is utilized, because, since the active hydrogen is contained in the $-SO_2OH$ group, the higher molecular weight alkyl groups merely dilute the molybdenum-containing composition, and increase the cost of the additive when finally incorporated.

Representative sulfonic acid compounds can contain hydrocarbon chains having alkyl or alkaryl groups as simple as methyl or ethyl groups or can comprise polymers having 8–200 carbon atoms, such as polyethylene having 30–50 carbon atoms. Oligomers, as for example, of propylene and butene, can be useful herein as alkyl groups. Naphthalene-based sulfonic acid compounds such as naphthalene-2,7-disulfonic acid, alpha-naphthalenesulfonic acid, 1-naphthol-4-sulfonic acid and 1-naphthylamine-3,8-disulfonic acid can also be used. Sulfonic acid compounds having an alkyl-benzene group have been found to be particularly useful in the present invention. Terpolymers, such as ethylene-propylene terpolymers, can also be used herein as alkyl groups.

Briefly, the sulfonic acid compound is reacted with the molybdenum halide, the reaction product of which is preferably hydrolyzed with water, producing a molybdenum sulfonate. The molybdenum sulfonate is then sulfurized to produce the additive of the present invention.

The sulfonic acid compound is reacted with the molybdenum halide with or without the presence of a solvent at a temperature of from 30° F. to 300° F. The molybdenum compounds disclosed are soluble in a solvent such as hexane or xylene, which may serve as a control for the reaction rate by reducing the solution viscosity and lowering the reflux temperature. If a solvent is used to react the sulfonic acid and molybdenum halide, the reaction occurs readily even at ambient temperature due to the homogeneous nature of the reactants. If no solvent is used, the reaction will occur at room temperature, although at a much slower rate. Applicant has found that the use of a solvent does not appreciably affect the incorporation of molybdenum into the additive of the present invention, regardless of whether the molybdenum halide is first dissolved in the solvent and then added to the sulfonic acid, or whether the molybdenum halide is added to a mixture of the sulfonic acid and solvent.

Upon addition of a molybdenum halide such as molybdenum pentachloride, to the sulfonic acid compound, a molybdenum sulfonate is formed and hydrogen halide, such as hydrogen chloride, is evolved in an exothermic reaction. The residual chloride concentration in the final product is dependent upon the sulfonic acid to molybdenum halide ratio, and in reaction conditions may vary from as low as 0.10 to as high as almost 10.0 weight per cent. It has been found that with a sulfonic acid: molybdenum pentachloride molar ratio of 5:1, approximately 0.47 per cent by weight of the reaction product is chloride. With a mole ratio of 3:1, approximately 2 weight per cent of the reaction product is chloride and with a mole ratio of 1:1, approximately 8.6 weight percent is chloride. Due to the corrosive nature of chlorine in an automobile engine, reduction of chloride concentration to as low a level as possible is desirable. Therefore, the reaction product of the reaction noted above is preferably hydrolyzed with water in order to remove as much chloride as possible. At least one mole of water is added for each chlorine molecule remaining in the molybdenum sulfonate. Preferably, excess water is added in order to assure maximum chloride removal, the excess water being easily removed with heat. The hydrolysis of the chlorine is an exothermic reaction which requires no additional application of heat, other than to remove excess water, if any, after the hydrolysis has been completed.

More specifically, molybdenum pentachloride can be added to a solution of alkyl benzene sulfonic acid and hexane over a 15-minute period at ambient temperatures, the reaction being written as:

$$n(ArSO_3H) + MoCl_5 \rightarrow (ArSO_3)_nMoCl_{(5-n)} + nHCl$$

From one to five moles of alkyl benzene sulfonic acid per mole of molybdenum halide, or more, can be used to produce the additive of the present invention. Due to the expense of the sulfonic acid, being the primary reactant in terms of quantity, the mole ratio and therefore the quantity of the sulfonic acid should preferably be as small as practicable while yielding effective molybdenum additives. Therefore, the 1:1 mole ratio of sulfonic acid to molybdenum pentachloride may be preferable, with the high residual chloride concentration in the reaction product being thereafter hydrolyzed with water, i.e.

$$(ArSO_3)_nMoCl_{(5-n)} \xrightarrow{H_2O} (ArSO_3)_nMoO_{\frac{(5-n)}{2}} + 5-n\,HCL.$$

The sulfur-containing compounds useful in the sulfurization reaction herein can be any compound which, when reacted with the molybdenum sulfonate resulting from the sulfonic acid-molybdenum halide reaction, produces what Applicants believe to be a thiomolybdenum sulfonate, i.e.,

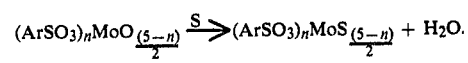

$$(ArSO_3)_nMoO_{\frac{(5-n)}{2}} \xrightarrow{S} (ArSO_3)_nMoS_{\frac{(5-n)}{2}} + H_2O.$$

The reaction product can be rewritten $(ArSO_3)_x MoS_y$, wherein X is an integer from 1 to 5 and Y is an integer from 1 to 5, and preferably from 1 to 3. Compounds such as elemental sulfur, hydrogen sulfide, ammonium sulfide, sodium sulfide and the alkyl polysulfides can serve as suitable sulfur sources. Elemental sulfur is preferred due to ease of handling and low expense. When hydrogen sulfide is used as a sulfur source, it is readily absorbed by the molybdenum sulfonate at ambient temperature and pressure. It is believed that sulfur is incorporated into the molybdenum sulfonate to form a thiomolybdenum sulfonate by displacement of an oxygen with sulfur.

The above described reaction products of the present invention are effective additives for lubricating oil compositions when added thereto in amounts to impart from 0.01 to 1.0 weight percent molybdenum based upon the lubricating oil, and preferably from 0.02 to 0.05 weight percent molybdenum. Suitable lubricating base oils are mineral oils, petroleum oils, synthetic lubricating oils such as those obtained by polymerization of hydrocarbons and other well known synthetic lubricating oils, and lubricating oils of animal and vegetable origin. Concentrates of the additive composition of the present invention in a suitable base oil containing about 0.3 to 30 weight per cent of the additive based upon the oil alone or in combination with other well known additives can be used for optimal additive blends.

The additives of this invention are often evaluated for friction modification using the Shell 4-Ball test and a motored engine test. In the Shell 4-Ball test, four steel balls are arranged tetrahedrally, with the lower 3 balls fixed in place and the upper ball rotating thereagainst in a chuck. The lower 3 balls are immersed in the lubricant under consideration and forced against the rotating upper ball, with the coefficient of friction being determined from the lateral force exerted on the stationary 3 ball arrangement.

In the motored engine test, an internal combustion automobile engine is driven by an electric motor. The engine oil is heated by friction to a given temperature similar to the operating temperature of the engine under various operating conditions. The amount of horsepower needed by the electric motor to overcome the friction between the moving parts in the automobile engine is measured. An effective friction modifier in the lubricating oil reduces the horsepower load on the electric motor, so that in Table III below, the lower the horsepower, the better the friction-reducing capabilities of the additive. The additive of the present invention was added to a 7½ W-30 crankcase oil for this test.

The invention will be more fully understood by reference to the following specific examples illustrating various modifications of the invention, which should not be construed as limiting the scope of the invention.

EXAMPLE 1

A 500 milliliter 3-neck round bottom flask equipped with a reflux condenser, thermostat, mechanical mixing and nitrogen purge tube was charged with a solution of 100 grams of hexane and 250 grams sulfonic acid. The sulfonic acid used herein is a 90% active alkyl benzene sulfonic acid in an oil diluent, with the alkyl group being a polypropylene having a molecular weight of approximately 500. To this mixture was added 23.8 grams of molybdenum pentachloride in a hexane solution over a 15-minute time period in order to reduce foaming. The mixture was heated to 260° F. over one hour to remove the solvent and volatiles and then cooled to 200° F. and held at that temperature for one hour. A 3-gram portion of water was added for hydrolysis, and the temperature increased to 250° F. to remove excess water.

EXAMPLE 2

To a 500-milliliter flask equipped as in Example 1, 250 grams of sulfonic acid (SA-119) in 100 grams of hexane was added, and a 39.7-gram portion of molybdenum pentachloride was intermixed over a 15-minute period. A nitrogen blanket was maintained while the mixture was brought to reflux, and the reflux was maintained for 3 hours as the hexane was distilled. A 6-gram portion of water was added, and the temperature increased to 250° F. as excess water, solvent and volatiles were removed.

EXAMPLE 3

The additive of this example was synthesized as in Example 2 with the exception that 200 grams of the sulfonic acid (SA-119) of Example 1 and a 95-gram portion of molybdenum pentachloride were used, and 25 grams of water was added for hydrolysis. Additionally, the resulting product was diluted with 162 grams of SX-5, a 110 neutral mineral oil to attain the desired viscosity.

EXAMPLE 4

102 grams of the reaction product of Example 1 was added to 98 grams of SX-5, and hydrogen sulfide gas bubbled through the solution.

EXAMPLE 5

103 grams of the reaction product of Example 2 was added to 97 grams of SX-5, and hydrogen sulfide gas bubbled through the solution.

EXAMPLE 6

188 grams of the reaction product of Example 3 was added to 12 grams of SX-5, and hydrogen sulfide gas bubbled through the solution.

Hydrogen sulfide ($H_2S$) was added at ambient temperature and pressure, the addition continuing as long as hydrogen sulfide was absorbed by the reaction products of Examples 1-3. Addition of hydrogen sulfide was terminated when hydrogen sulfide was evolved from the reaction vessel.

TABLE I

| Example No. | gm Alkyl Benzene Sulfonic Acid (ABSA) | gm MoCl$_5$ | gm SX-5 | Moles ABSA/ MoCl$_5$ | % Mo | % Cl | % S | % S from ABSA |
|---|---|---|---|---|---|---|---|---|
| 1 | 250 | 23.8 | — | 5 | 3.3 | 0.19 | | |
| 2 | 250 | 39.7 | — | 3 | 5.3 | 0.70 | | |
| 3 | 200 | 95.0 | 162 | 1 | 7.7 | 2.10 | | |
| 4 | | | | | | | 3.9 | 2.8 |

TABLE I-continued

| Example No. | gm Alkyl Benzene Sulfonic Acid (ABSA) | gm MoCl5 | gm SX-5 | Moles ABSA/MoCl5 | % Mo | % Cl | % S | % S from ABSA |
|---|---|---|---|---|---|---|---|---|
| 5 | | | | | | | 4.7 | 2.8 |
| 6 | | | | | | | 8.9 | 2.8 |

TABLE II

| *Example No. | SHELL 4-BALL TEST M/Mo* at load in Kg | | | % Mo in Blend |
|---|---|---|---|---|
| | 20 | 30 | 40 | |
| 1 | 0.57 | 0.63 | 0.60 | 0.043 |
| 2 | 0.57 | 0.62 | 0.65 | 0.044 |
| 3 | 0.65 | 0.65 | 0.52 | 0.042 |
| 4 | 0.60 | 0.59 | 0.52 | 0.043 |
| 5 | 0.68 | 0.56 | 0.58 | 0.044 |
| 6 | 0.80 | 0.83 | 0.65 | 0.042 |

Test Parameters: 1800 rpm, 250° F., 10 minutes per load
*Coefficient of friction of oil with molybdenum additive divided by coefficient of friction of baseline oil without additive.

TABLE III

| | MOTORED ENGINE TEST Friction Horsepower at °F. | | | | | | |
|---|---|---|---|---|---|---|---|
| | 100° | 140° | 180° | 200° | 220° | 240° | 260° |
| Example No. 6 | 11.05 | 9.70 | 8.90 | 8.75 | 8.70 | 8.80 | 9.25 |
| Example No. 3 | 11.30 | 9.85 | 9.00 | 8.75 | 8.70 | 8.85 | 9.30 |
| Baseline oil | 11.25 | 9.90 | 9.10 | 8.85 | 8.80 | 9.05 | 9.50 |

We claim:

1. An oil soluble lubricating oil composition comprising a sulfurized molybdenum sulfonate in a lubricating oil, wherein said molybdenum sulfonate is the sulfurized reaction product of molybdenum halide and a hydrocarbyl sulfonic acid compound, the reaction product of molybdenum halide and a hydrocarbyl sulfonic acid compound having been prepared by reacting said molybdenum halide with said hydrocarbyl sulfonic acid compound at a temperature within the range of 30° F. to 300° F.

2. The composition of claim 1 wherein said hydrocarbyl sulfonic acid compound comprises an alkaryl sulfonic acid having an alkyl group containing from 8 to 200 carbon atoms.

3. The composition of claims 1 or 2 wherein the molybdenum halide comprises molybdenum pentachloride.

4. The composition of claim 1 wherein the hydrocarbyl sulfonic acid compound comprises alkyl benzene sulfonic acid.

5. The composition of claim 1 wherein the molybdenum sulfonate is sulfurized by elemental sulfur, hydrogen sulfide, ammonium sulfide, sodium sulfide, alkyl polysulfide, or other sulfur-yielding compound.

6. The composition of claim 1 wherein the sulfurized molybdenum sulfonate is incorporated in a lubricating oil at a concentration to impart from 0.01 to 1.0 percent molybdenum by weight of the lubricating oil.

7. A process for preparing a lubricating oil composition having improved friction modifying properties comprising:
   (a) reacting a hydrocarbyl sulfonic acid compound and molybdenum halide at a temperature within the range of 30° F. to 300° F. to form molybdenum sulfonate,
   (b) reacting said molybdenum sulfonate with sulfur or a sulfur-yielding compound, and
   (c) combining the oil soluble reaction product of step (b) with a lubricating oil.

8. The process of claim 7 wherein said hydrocarbyl sulfonic acid compound comprises an alkaryl sulfonic acid having an alkyl group containing from 8 to 200 carbon atoms.

9. The process of claim 7 or 8 wherein said molybdenum halide comprises molybdenum pentachloride.

10. The process of claim 7 wherein said hydrocarbyl sulfonic acid compound comprises alkyl benzene sulfonic acid.

11. The process of claim 7 wherein said sulfur-yielding compound comprises hydrogen sulfide, ammonium sulfide, sodium sulfide, alkyl polysulfide, or elemental sulfur.

* * * * *